United States Patent [19]

Maleski et al.

[11] Patent Number: 6,034,276

[45] Date of Patent: Mar. 7, 2000

[54] PROCESS FOR PREPARING 1-CHLORO-2,4-DIAMINOBENZENE

[75] Inventors: Robert Joseph Maleski, Kingsport; Edward Tipton Mullins, Mount Carmel, both of Tenn.

[73] Assignee: Eastman Chemical Company, Kingsport, Tenn.

[21] Appl. No.: 09/274,464

[22] Filed: Mar. 22, 1999

[51] Int. Cl.[7] .................................................. C07C 209/00
[52] U.S. Cl. ...................... 564/417; 564/416; 564/420; 564/421; 564/422
[58] Field of Search .................................. 564/416, 417, 564/420, 421, 422

[56] References Cited

U.S. PATENT DOCUMENTS

| | | |
|---|---|---|
| 3,073,865 | 1/1963 | Spiegler . |
| 3,149,161 | 9/1964 | Graham et al. . |
| 3,350,452 | 10/1967 | Rylander et al. . |
| 3,361,819 | 1/1968 | Kosak et al. . |
| 3,474,144 | 10/1969 | Craig et al. . |
| 3,666,813 | 5/1972 | Hindlin et al. . |
| 3,928,451 | 12/1975 | Krishnan . |
| 3,989,756 | 11/1976 | Fujine et al. . |
| 4,059,627 | 11/1977 | Kritzler et al. . |
| 4,070,401 | 1/1978 | Hirai et al. . |
| 4,375,550 | 3/1983 | Bird et al. . |
| 4,929,737 | 5/1990 | Lentz et al. . |
| 4,960,936 | 10/1990 | Baumeister et al. . |
| 5,663,434 | 9/1997 | Maleski . |
| 5,689,021 | 11/1997 | Cordier et al. . |

FOREIGN PATENT DOCUMENTS 1191610  5/1970  United Kingdom .

OTHER PUBLICATIONS

Vogel's Textbook of Practical Organic Chemistry, 5th Edition, Addision Wesley Longman Limited, Essex England, p. 451 (1989).

*Primary Examiner*—Paul J. Killos
*Attorney, Agent, or Firm*—Michael J. Blake; Harry J. Gwinnell

[57] ABSTRACT

Disclosed is an improved process for preparing 1-chloro-2, 4-diaminobenzene by the selective hydrogenation of 1-chloro-2,4-dinitro-benzene wherein the hydrogenation is carried out in the presence of a modified Raney nickel catalyst containing about 70 to 95 weight percent nickel, about 4 to 10 weight percent aluminum, about 0.1 to 4 weight percent molybdenum, and from 0 to about 20 weight percent cobalt. The 1-chloro-2,4-diaminobenzene is useful as an intermediate for disperse dyes and for color photography.

7 Claims, No Drawings

PROCESS FOR PREPARING 1-CHLORO-2,4-DIAMINOBENZENE

PROCESS FOR PREPARING 1-CHLORO-2,4-DIAMINOBENZENE

This invention pertains to a novel process for the preparation of 1-chloro-2,4-diaminobenzene by the catalytic hydrogenation of 1-chloro-2,4-dinitrobenzene. More specifically, this invention pertains to the preparation of 1-chloro-2,4-diaminobenzene by hydrogenating 1-chloro-2,4-dinitrobenzene in the presence of a modified Raney nickel catalyst comprising as essential components a major portion of nickel and minor portions of aluminum and molybdenum and, optionally, cobalt. The 1-chloro-2,4-diaminobenzene produced in accordance with the present invention may be selectively acylated to produce N-(3-amino-4-chlorophenyl) acylamides which are useful as intermediates for color photography and for preparing disperse dyes for textile fibers. See, for example, U.S. Pat. No. 5,663,434.

The catalytic reduction of 1-chloro-2,4-dinitrobenzene using known, commercially-available catalysts gives low yields of the corresponding diamine and generates harmful by-products. The hydrogenation of halogen-containing mono- and di-nitrobenzenes to the corresponding halo(amino)benzene and halo(diamino)benzene compounds presents long standing problems such as, for example, catalyst deactivation, dehalogenation of the starting material, low yields and by-product formation. Various catalysts and catalyst systems have been developed for the purpose of overcoming one or more of the above-mentioned problems. U.S. Pat. No. 3,073,865 discloses the use of a platinum-on-carbon catalyst in combination with a dehalogenation-suppressor such as MgO and $Mg(OH)_2$. U.S. Pat. No. 3,149,161 describes the use of certain platinum- on-carbon and palladium-on-alumina catalysts and U.S. Pat. No. 3,350,452 discloses the use of platiunum-on-barium carbonate or strontium carbonate. The use of a platiunum-on-carbon catalyst in the presence of a phosphite compound is disclosed in U.S. Pat. No. 3,474,144 whereas the use of a platinum-on-carbon catalyst in combination with various amines to inhibit dechlorination is disclosed in U.S. Pat. No. 3,361,819. U.S. Pat. No. 3,666,813 describes platinum and palladium catalysts modified by one or more metals selected from lead, bismuth and silver. The use of catalysts comprising platinum, palladium, rhodium, iridium, ruthenium or osmium deposited on carbon and activated with a phosphoric acid or salt is described in U.S. Pat. No. 4,375,550. U.S. Pat. No. 4,059,627 describes the use of noble metal catalysts on carbon in the presence of thioethers. The use of platinum catalysts in the presence of primary amines is disclosed in U.S. Pat. No. 4,070,401. British Patent 1,191610 discloses a process utilizing a Raney nickel catalyst in combination with a thiocyanate compound. The use of a chromium-containing, Raney cobalt catalyst is disclosed in U.S. Pat. No. 4,929,737 and PCT Published Patent Application WO 89/07096. The use of Raney nickel-type catalysts modified with a large amount, e.g., 5 to 15%, of molybdenum is described in U.S. Pat. No. 5,689,021.

The preparation of 1-chloro-2,4-diaminobenzene by the catalytic hydrogenation of 1-chloro-2,4-dinitrobenzene is particularly difficult due to the above mentioned problems of catalyst deactivation, dehalogenation of the starting material, low yields and by-product formation plus additional unidentified side reactions. U.S. Pat. No. 3,928,451 discloses the hydrogenation of 1-chloro-2,4-dinitrobenzene to the corresponding halodiamine using a specific platinum on granular carbon catalyst in the presence of esters as solvents. Moderate yields, e.g., about 60% by weight, are achieved with considerable by-product formation. The use of Raney nickel in the presence of dehalogenation inhibitors also has been claimed to be an effective catalyst system for the preparation of 1-chloro-2,4-diaminobenzene from 1-chloro-2,4-dinitrobenzene. For example, U.S. Pat. No. 3,989,756 discloses the combination of Raney nickel and dicyandiamide, cyanamide or calcium cyanamide. U.S. Pat. No. 4,960,936 claims the same catalyst in combination with a formamidine salt. The use of any of these dehalogenation inhibitors increases significantly the cost of the hydrogenation process and complicates the purification of the final product.

Many of the catalysts and catalyst systems described above are designed for specific cases, lose catalyst activity, do not have general application, or do not give consistent results in batch operation, depending upon not only the halonitroaromatic starting material but the purity or grade starting material. Thus, a need exist for an improved catalyst which may be used for the efficient hydrogenation of 1-chloro-2,4-dinitrobenzene to 1-chloro-2,4-diaminobenzene in improved yields and/or purity.

We now have discovered that 1-chloro-2,4-diaminobenzene can be prepared in improved yields and purity by hydrogenating 1-chloro-2,4-dinitrobenzene in the presence of a modified Raney nickel catalyst comprising as essential components about 70 to 95 weight percent nickel, about 4 to 10 weight percent aluminum, about 0.1 to 4 weight percent molybdenum, and from 0 to about 20 weight percent cobalt. The present invention therefore provides a process for the preparation of 1-chloro-2,4-diaminobenzene which comprises contacting 1-chloro-2,4-dinitrobenzene with hydrogen in the presence of a modified Raney nickel catalyst comprising as essential components about 70 to 95 weight percent nickel, about 4 to 10 weight percent aluminum, about 0.1 to 4 weight percent molybdenum, and from 0 to about 20 weight percent cobalt under hydrogenation conditions of temperature and pressure. The improved process provides the desired 1-chloro-2,4-diaminobenzene in high yields and without having to employ expensive and time consuming purification techniques to remove unwanted impurities which are produced when conventional Raney nickel catalysts are used. The use of additives, such as those mentioned above in the prior art, to prevent dehalogenation or generation of other by-products is not necessary and thus the process of the invention is carried out in the substantial absence of dehalogenation inhibitors such as dicyandiamide, cyanamide, calcium cyanamide, and formamidine salts. Our novel process can be carried out successfully using only the modified Raney nickel catalyst to produce the desired 1-chloro-2,4-diaminobenzene in high yield and purity.

The catalyst utilized in the present invention may be prepared according to known techniques and/or may be purchased from Grace Davison. The general method for catalyst preparation is described in various textbooks such as, for example, *Vogel's Textbook of Practical Organic Chemistry*, 5th Edition, Addision Wesley Longman Limited, Essex, England, page 451. The catalyst employed in the present invention preferably consists essentially of about 90 to 95 weight percent nickel, about 4 to 8 weight percent aluminum, about 0.5 to 3 weight percent molybdenum. Particularly useful catalysts are available from Grace Davison under the designations Grace Davison Raney Nickel, Grade R3110 and Grade R4310.

The catalytically-effective amount of the modified Raney nickel catalyst used in the novel process of our invention may vary depending upon several factors such as temperature, pressure, solvent, reaction time, purity of the starting 1-chloro-2,4-dinitrobenzene, and the activity of the particular catalyst used. Usually, however, the amount of catalyst used in batch operations is the range of 0.01–10.0 weight percent based on the weight of the 1-chloro-2,4-dinitrobenzene reactant with the preferred range being about 0.1 to 5.0 weight percent. As will be apparent to those skilled in the art, the catalyst:reactant weight ratio is indeterminable in continuous operation wherein 1-chloro-2,4-dinitrobenzene reactant is continuously fed or added to, and 1-chloro-2,4-diaminobenzene product is continuously removed from, a reaction zone containing a slurry or fixed bed of catalyt. The physical form of the catalyst may vary from a powder or granular form for slurry operation of the hydrogenation process to pellets or extrudates suitable for use in fixed beds of the catalysts.

The hydrogenation conditions of pressure and temperature may be varied considerably, with the particular temperature and/or pressure used being dependent upon the such variable factors as catalyst concentration, solvents used, and desired reaction times. The process may be carried out at temperatures in the range of about 25 to 125° C. with temperatures in the range of about 40–80° C. being preferred. The temperature and solvents are normally chosen to ensure complete solubility of the starting 1-chloro-2,4-diaminobenzene While the process may be operated at total pressures over the range of about 100 to 1500 pounds per square inch gauge (psig), it preferably is operated at a total pressure in the range of about 500 to 1000 psig, most preferably at a pressure in the range of about 600 to 800 psig.

The hydrogenation process preferably is carried out in the presence of an inert (nonreactive) organic solvent, preferably in one or more hydroxylic solvents such as alkanols having the structure R—OH, ethylene glycol ethers having the structure ROCH$_2$CH$_2$OH, propylene glycol ethers having the structure ROCH$_2$CH(CH$_3$)OH or diethylene glycol ethers having the structure R—O(CH$_2$CH$_2$O)$_2$H, wherein R represents a C$_1$–C$_4$, straight- or branched-chain, alkyl group. Alkanols such as methanol, ethanol, and isopropanol and mixtures of any two or more thereof constitute the preferred solvent. Other organic solvents which may be employed include carboxylate esters such as methyl and ethyl acetate; ethers such as tetrahydroforan and diisopropyl ether; and aprotic polar solvents such as N,N-dialkylformamides and N,N-dialkylacetamides, e.g., N,N-dimethyl-formamide and N,N-dimethylacetamide, and to a lesser extent aromatic hydrocarbons such as toluene and aliphatic hydrocarbons such as heptane. Some of these latter mentioned solvents may be used as co-solvents in combination with the alkanols. The presence of significant amounts of water in the reaction mixture appears to have a detrimental effect on the results of the hydrogenation process. Accordingly, the process preferably is carried out under substantially anhydrous conditions, e.g., the amount of water present should not exceed about 10 weight percent, preferably not about 2 weight percent, based on the total weight of the reaction mixture.

The process of the present invention may be carried out as a batch, semi-continuous, or continuous process. In a batch process, a slurry of the catalyst is added to the stirred pressure vessel in an inert solvent, preferably the solvent used to dissolve the starting 1-chloro-2,4-dinitro-benzene. After pressurization with hydrogen to the desired pressure, the reaction vessel is heated to the chosen reaction temperature. After complete hydrogenation, the reaction mixture is removed from the pressure vessel and the catalyst separated by filtration. The product may be isolated from the filtrate or in some cases further reacted without isolation from the solvent. In a continuous process a fixed bed catalyst using a larger particle size can be utilized. The catalyst bed may be located in a pressure vessel and a solution of the reactant slowly fed continuously above the bed at elevated temperature and pressure while the 1-chloro-2,4-diamine solution is removed at the bottom of the pressure vessel. In another mode of continuous operation, a slurry of catalyst is agitated in a pressure vessel fitted with a filter leg to permit continuous removal of a solution of the product in the inert solvent. The reactant solution is fed continuously as the product solution is continuously removed.

The process provided by this invention is further illustrated by the following examples. The percentages given in the examples are by weight unless specified otherwise.

EXAMPLE 1

A mixture of 1-chloro-2,4-dinitrobenzene (40.0 g, 0.197 mole), methanol (100 g), and 3.0 g of modified Raney nickel catalyst consisting of about 83.1% Ni, 9.3% Co, 7.1% Al and 0.5% Mo was charged into an autoclave. The autoclave was sealed, pressurized with hydrogen to 700 psig, and the hydrogenation carried out at about 30° C. Hydrogen uptake was observed by monitoring the pressure change. After the hydrogen uptake ceased (approximately 6.0 hrs.), the reaction mixture was heated for a short time longer and then the autoclave was vented. A sample of the reaction mixture was taken and analyzed by liquid chromatography after being separated from the solid catalyst. The desired product 1-chloro-2,4-diaminobenzene was formed in high yield and good purity. Liquid chromatography indicated an area % of 92.4% (excluding the methanol solvent) for the product. Very little dechlorination had occurred.

EXAMPLE 2

Example 1 was repeated exactly except the reaction temperature was increased to about 40° C., a hydrogen pressure of about 500 psig was used and the modified Raney Ni catalyst (3.0 g) used consisted of about 85.7% Ni, 9.0% Co, 4.1% Al and 1.2% Mo. The hydrogenation time was approximately 2.5 hrs. Liquid chromatography showed an area % of 92.5% (excluding the methanol solvent) for the desired 1-chloro-2,4-diaminobenzene.

EXAMPLE 3

Example 2 was repeated except that the modified Raney Ni catalyst used contained about 87.7% Ni, 5.3% Co, 5.7% Al and 1.3% Mo. Reaction time was about 3.0 hrs. Liquid chromatography showed an area % of 87.0% (excluding the methanol solvent) for the desired 1-chloro-2,4-diaminobenzene.

EXAMPLE 4

Example 2 was repeated except that the modified Raney Ni catalyst used contained about 82.3% Ni, 11.3% Co, 4.9% Al and 1.5% Mo. Reaction time was about 4.0 hrs. Liquid chromatography showed an area % of 92.0% (excluding the methanol solvent) for the desired 1 -chloro-2,4-diaminobenzene.

EXAMPLE 5

Example 2 was repeated except the modified Raney Ni catalyst used contained about 73.2% Raney Ni, 18.9% cobalt, 5.0% aluminum and 2.9% Mo. The reaction time was about 3.5 hrs. Liquid chromatography shown an area % of 88.8% (excluding the methanol solvent) for the desired 1-chloro-2,4-diaminobenzene.

EXAMPLE 6

Example 2 was repeated except that the solvent used was a mixture of methanol (50.0 g) and isopropanol (50.0 g). The reduction time was 4.0 hours. Liquid chromatography showed an area % of 83.3% (excluding the solvent) for the desired 1-chloro-2,4-diaminobenzene.

EXAMPLE 7

Example 2 was repeated except that the solvent used was a mixture of methanol (50.0 g) and toluene (50.0 g). The reduction time was 3.5 hours. Liquid chromatography showed an area % of 85.2% (excluding the solvent) for the desired 1-chloro-2,4-diaminobenzene.

COMPARATIVE EXAMPLE 1

A mixture of 1-chloro-2,4-dinitrobenzene (41.0 g, 0.202 m), methanol (95.0 g) and unmodified Raney nickel catalyst (3.0 g; Grace Davison) was charged into an autoclave. The autoclave was sealed, pressurized with hydrogen to 900 psig and the hydrogenation carried out at 40–45° C. Hydrogen uptake was observed by monitoring the pressure change. After the hydrogen uptake ceased (approximately 5.0 hours), the mixture was heated for a short time longer and then the autoclave was vented. A sample of the reaction mixture was taken and analyzed by liquid chromatography after being separated from the solid catalyst. Liquid chromatography indicated an area % of 62.4% (excluding the methanol solvent) for the 1-chloro-2,4-diaminobenzene with a multiplicity of impurities being formed, including m-phenylenediamine, resulting from dechlorination. In contrast to Examples 1-7 of the present invention using a modified Raney Ni catalyst, this Comparative Example 1 resulted in the formation of more impurities and a much lower yield of desired 1-chloro-2,4-diaminobenzene.

COMPARATIVE EXAMPLES 24

Example 1 was repeated using the following modified nickel catalyst compositions:
Comparative Example 2: 87.2% Ni, 0.1% Co, 8.2% Al, 2.3% Cr, 2.2% Fe.
Comparative Example 3: 78.5% Ni, 7.6% Co, 10.3% Al, 3.6% Cr.
Comparative Example 4: 78.1% Ni, 8.5% Co, 8.9% Al, 0.1% Mo, 4.4% Cr.

The amount of 1-chloro-2,4-diaminobenzene (GC area percent excluding methanol solvent) obtained in these comparative examples was
Comparative Example 2—38.1%; Comparative Example 3—17.1%;
Comparative Example 4—5.9%. These examples show that the presence of Fe and Cr in the catalyst formulations is detrimental to the performance of the catalyst in the hydrogenation of 1-chloro-2,4-dinitrobenzene to 1-chloro-2,4-diaminobenzene.

The invention has been described in detail with particular reference to preferred embodiments thereof, but it will be understood that variations and modifications will be effected within the spirit and scope of the invention.

We claim:

1. Process for the preparation of 1-chloro-2,4-diaminobenzene which comprises contacting 1-chloro-2,4-dinitrobenzene with hydrogen in the presence of a modified Raney nickel catalyst comprising as essential components about 70 to 95 weight percent nickel, about 4 to 10 weight percent aluminum, about 0.1 to 4 weight percent molybdenum, and from 0 to about 20 weight percent cobalt under hydrogenation conditions of temperature and pressure.

2. Process according to claim 1 wherein the hydrogenation conditions comprise a temperature in the range of about 25 to 125° C. and a pressure in the range of about 100 to 1500 pounds per square inch gauge.

3. Process according to claim 2 wherein the process is carried out in the presence of an inert solvent comprising one or more hydroxylic solvents selected from alkanols having the structure R—OH, ethylene glycol ethers having the structure $ROCH_2CH_2OH$, propylene glycol ethers having the structure $ROCH_2CH(CH_3)OH$ or diethylene glycol ethers having the structure $R—O(CH_2CH_2O)_2H$, wherein R represents a $C_1$-$C_4$, straight- or branched-chain, alkyl group.

4. Process for the preparation of 1-chloro-2,4-diaminobenzene which comprises contacting 1-chloro-2,4-dinitrobenzene with hydrogen in the presence of a modified Raney nickel catalyst consisting essentially of about 90 to 95 weight percent nickel, about 4 to 8 weight percent aluminum, about 0.5 to 3 weight percent molybdenum at a temperature in the range of about 25 to 125° C. and a pressure in the range of about 100 to 1500 pounds per square inch gauge.

5. Process according to claim 4 wherein the process is carried out in the presence of an inert solvent comprising one or more hydroxylic solvent selected from alkanols having the structure R—OH, ethylene glycol ethers having the structure $ROCH_2CH_2OH$, propylene glycol ethers having the structure $ROCH_2CH(CH_3)OH$ or diethylene glycol ethers having the structure $R—O(CH_2CH_2O)_2H$, wherein R represents a $C_1$-$C_4$, straight- or branched-chain, alkyl group.

6. Process according to claim 4 wherein the process is carried out at a temperature in the range of about 40 to 80°C. and a pressure in the range of about 100 to 1500 pounds per square in gauge.

7. Process according to claim 4 wherein the process is carried out at a temperature in the range of about 40 to 80° C. and a pressure in the range of about 100 to 1500 pounds per square inch gauge and in the presence of an inert solvent selected from methanol, ethanol, isopropanol and mixtures of any two or more thereof.

* * * * *